United States Patent [19]

Reddemann et al.

[11] Patent Number: 5,073,947

[45] Date of Patent: Dec. 17, 1991

[54] HEARING DEVICE FOR A PROTECTIVE HELMET

[75] Inventors: Hans Reddemann; Tronje von dem Hagen, both of Lübeck, Fed. Rep. of Germany; Balz Knabenhans, Ennetbürgen, Switzerland

[73] Assignee: Drägerwerk AG, Lübeck, Fed. Rep. of Germany

[21] Appl. No.: 425,696

[22] Filed: Oct. 23, 1989

[30] Foreign Application Priority Data

Oct. 22, 1988 [DE] Fed. Rep. of Germany ....... 3836036

[51] Int. Cl.[5] ........................ H04R 25/00; A61B 7/02

[52] U.S. Cl. .................................. 381/187; 381/68.6; 381/69; 181/135

[58] Field of Search ............... 455/602, 617, 606, 351; 381/68.6, 69, 74, 151, 183, 187, 72, 68.4, 68.2; 379/430; 128/420.6; 181/135

[56] References Cited

U.S. PATENT DOCUMENTS

| | | | |
|---|---|---|---|
| 3,088,002 | 4/1963 | Heisig | 381/187 |
| 3,190,973 | 6/1965 | Aileo | 381/187 |
| 3,512,088 | 5/1970 | Ross | 381/74 |
| 3,752,939 | 8/1973 | Bartz | 128/420.6 |
| 4,150,262 | 4/1979 | Ono | 381/68.6 |
| 4,152,553 | 5/1979 | White | 379/430 |
| 4,334,315 | 6/1982 | Ono et al. | 381/151 |
| 4,633,498 | 12/1986 | Warnke et al. | 381/74 |
| 4,636,592 | 1/1987 | Scott | 381/187 |

*Primary Examiner*—James L. Dwyer

*Assistant Examiner*—Jason Chan

*Attorney, Agent, or Firm*—McGlew & Tuttle

[57] ABSTRACT

The invention concerns a hearing device for a protective helmet with a receiving deice for auditory signals, that at the very least are deliverable from the earphones arranged on the inner surface of the protective helmet. The invention has as its basic function to reduce the volume of the helmet contruction and the weight of the hearing device in relation to the usual construction, and to make the positioning of the earphones on the ears of the helmet wearer unnecessary. The purpose will be met in that the earphones in the outer auditory canal of the helmet wearer will be developed as importable earplugs. The auditory signals that are supplied by a receiving device consisting of a receiver and a coupled transmitter will be transmitted from the transmitter of the receiving device over a wireless transmission line that is integrated into the earplug-receiver of the earplug.

10 Claims, 1 Drawing Sheet

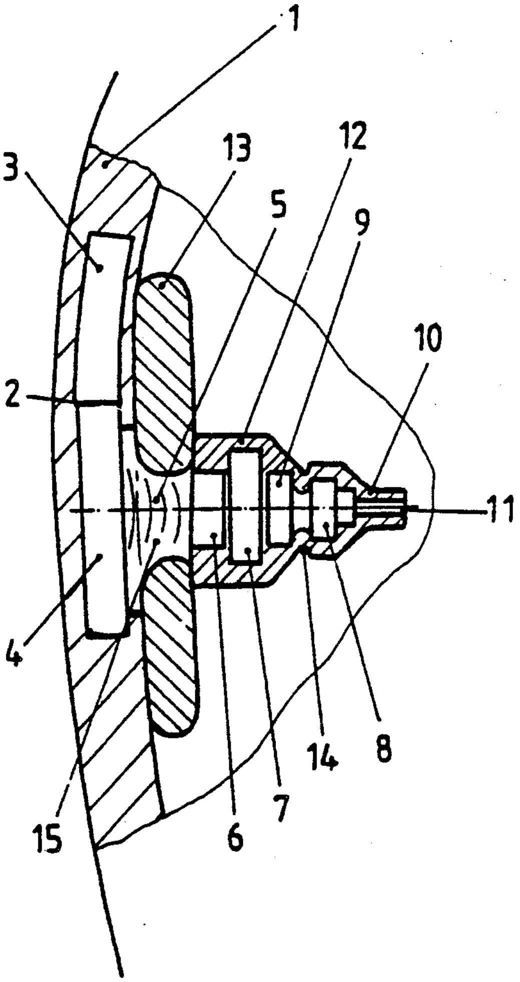
1
3
13
12
5
9
2
10
11
4
14
8
15
6
7

HEARING DEVICE FOR A PROTECTIVE HELMET

FIELD OF THE INVENTION

The invention consists of a hearing device for a protective helmet with a receiving device for auditory signals, which signals are deliverable on the inner surface earphones arranged in the protective helmet.

Such a hearing device makes it possible for the helmet wearer to hear acoustic signals or, as the case may be, radio telephone traffic from out of his vicinity. Simultaneously the hearing device can be so developed that the hearing of the helmet wearer is shielded from undesirable surrounding noises.

BACKGROUND OF THE INVENTION

From German Patent 31 37 113 a hearing device is known, whereby on the inside of the helmet noise muffling earflaps are arranged as earphones enclosing the ear muscles of the helmet wearer. The earphones are positionable on the ears of the helmet wearer, and transmit the desired auditory signals.

The earphones are connected with the signal source by a cable. A disadvantage of the described hearing device is the relatively large volume of the structural extension that is necessitated by the side lateral protrusion of the protective helmet or a reduction of the wall strength of the protective helmet in the area of the ear flaps. The large volume of the structural extension and the required noise repression features adds great weight to the head of the helmet wearer. After the helmet is attached the earphones must be positioned exactly on the ears of the helmet wearer.

SUMMARY AND OBJECTS OF THE INVENTION

It is an object of the invention to reduce both the volume of the structural extension and the weight of the hearing device and to make the positioning of the earphones on the ears of the helmet wearer unnecessary.

According to the invention a detached portable ear phone is provided in the outer auditory canal of the helmet wearer A receiver and a coupled transmitter are provided as a helmet receiving device, such that auditory signals may be transported from the transmitter of the receiving device over a wireless transmission line to a receiver on an earplug that is integrated into an earplug receiver.

The advantages obtained with the invention consist of a minimization of the hearing device with regard to the volume of the helmet structure and with regard to weight while at the same time shielding the helmet wearer from disturbing environmental noises, and providing a good coupling of the hearing device with the hearing of the helmet wearer. Through the wireless signal transmission from the transmitter of the receiving device on the earplug-receiver the earplug is free from disturbing cable connections and no electric plug connections would be needed. With this arrangement, the danger from an interruption of the auditory signal transmission would be reduced.

In a further development of the invention the transmitter and receiver of the receiving device are integrated into the protective helmet. The arrangement does not require a cable connection to the transmitter.

The transmission of auditory signals from the transmitter of the receiving device on the earplug-receiver can occur on inductive paths.

In a further development of the invention the transmission of auditory signals from the transmitter of the receiving device occurs on at the earplug-receiver so that the auditory signals can be modulated on infrared rays, on a high frequency carrier, or on ultrasonic vibrations.

The application of infrared radiation is especially appropriate in the present case in that the transmitter and receiver for infrared radiation are small and can easily be built and an infrared transmission line insolated against incoming radiation from electromagnetic jamming signals is especially unsusceptible to disturbances.

In a further development of the invention the earplug includes a soft plastic attachment piece, in which an electroacoustic transformer is contained, and an adapter piece in which the energy source, the amplification piece and the earplug-receiver are accommodated.

This arrangement provides the advantages that the attachment piece can be produced out of a soft plastic material which can be well adjusted to the auditory canal of the helmet wearer and can be fixed there, and that the adapter piece can be produced out of a solid material which lends to mechanical stability in the construction and makes the built-in components more secure. Through the divisibility of the adapter piece and attachment part, easier access to the built-in components is possible. In particular, a more simple alteration of the energy source is guaranteed The adapter piece can be placed on one of the interior walls of the protective helmet, facing the installed elastic buffer. Through this buffer the earplug can be fixed in the auditory canal of the helmet wearer and the ear drum and ear muscle of the helmet wearer can be mechanically protected.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only figure is a cross sectional view of the construction according to the invention.

DESCRIPTION OF THE PREFERRED EMBODIMENTS

Referring to the drawings in particular, the invention embodied therein comprises a hearing device for a protective helmet 1. The arrangement includes a receiving and transmitting device 2 which is connected to the helmet 1. The receiving and transmitting device receives signals representing auditory signals and transmits the signals. An earplug arrangement or earplug car phone and receiving unit 14 including a receiver 6 and an electro acoustic transformer or earphone 8 (earphone). The earplug arrangement 14 is positioned in the outer auditory canal 100 of the wearer. The receiving and transmitting device 2 (via the transmitter 3) cooperates with the earplug receiver 6 to define a transmission path 5 for transmitting signals representative of auditory signals from the receiving and transmitting device 2 to the earplug receiver 6.

The single illustration shows the protective helmet 1. The receiving device 2 that is integrated into the protective helmet 1 receives with its receiver 3 auditory signals out of a signal source that is not represented and that, for example, can be a radio telephone network. The receiver 3 provides signals through the transmitter 4 of the receiving device. Here the auditory signals will be modulated in the form of a ray 5 of infrared light. The infrared ray is directed to the earplug-receiver 6 that is provided as an infrared sensitive photodiode thereby providing a transmission line. The transmitter 4 is arranged in the shell of the helmet at ear's height of the helmet wearer who is not shown.

The earplug 14 is represented with the earplug receiver facing the inner surface of the helmet 1. In use it is inserted into the auditory canal 100 of the helmet wearer who is not shown.

The receiving signals are boosted in the amplification piece 7 and demodulated. The electroacoustic transformer or earphone 8 transforms the electric auditory signals into audible sound vibrations. A battery as an energy source supplies the electronic elements 6, 7, 8, with electrical energy. The soft plastic attachment piece 10 of the earplug earphone 14 fixes the earplug earphone 14 in the auditory canal of the helmet wearer who is not shown. Through the bore 11 in the attachment piece 10 the sound vibrations of the electroacoustic transformer 8 will lead to the eardrum of the helmet wearer. Because the attachment piece 10 seals off the auditory canal of the helmet wearer from the outside, it is ensured that disturbing environmental noises will be muffled.

The buffer 13 made out of soft plastic material that is arranged on the inner surface of the protective helmet 1 presses the set on protective helmet 1 on the attachment piece 12 of the earplug 14. Thereby a slipping out of the earplugs 14 out of the auditory canal of the helmet wearer will be avoided. Furthermore, the buffer 13 protects the ear area in contact with the device of the helmet wearer from mechanical burden.

An opening 15 in the buffer 13 makes possible a free propagation of the infrared rays 5 from the transmitter 4 of the transmission device 2 to the earplug-receiver 6.

While a specific embodiment of the invention has been shown and described in detail to illustrate the application of the principles of the invention, it will be understood that the invention may be embodied otherwise without departing from such principles.

What is claimed is:

1. A hearing device for a protective helmet, comprising:

a receiving device and a wireless transmitting device mounted within the helmet for receiving and transmitting auditory signals; and, an earplug arrangement including an earphone positioned in the outer auditory canal of the wearer and a wireless earplug receiver, said transmitting device and said earplug receiver being positioned spaced apart in facing relationship defining a wireless transmission path for transmitting signals representative of auditory signals from said transmitting device to said earplug receiver.

2. A hearing device according to claim 1, wherein said receiving device and said wireless transmitting device are formed as a part of a shell of said protective helmet.

3. A hearing device according to claim 2, wherein said transmitting device is an infrared transmitter, said earplug receiver is an infrared sensitive receiver, said transmission path to being an infrared transmission path.

4. A hearing device according to claim 2, wherein said transmission path between said transmitting device and said earplug receiver is a high frequency transmission path.

5. A hearing device according to claim 2, wherein said transmission path between said transmitting device and said earplug receiver is an ultrasonic transmission path.

6. A hearing device according to claim 2, wherein the earplug is positionable within the outer auditory canal of the helmet wearer and removable therefrom, said earplug including an electro-acoustic transducer coupled with an earplug attachment piece, an energy source, an amplification unit and a housing element containing said earplug receiver.

7. A hearing device according to claim 6, wherein an elastic buffer is positioned adjacent the receiver device the wireless and transmitting device in the helmet, the housing of said earplug bordering said elastic buffer when the helmet wearer head is positioned within the helmet.

8. A hearing device of the type completely enclosed within a protective shell of a helmet and comprising auditory signal receiving and transmitting devices mounted on the shell at a location between an outer surface of the shell and the ear of a user;

an earplug earphone and receiving unit including an attachment piece containing an electro-acoustic transducer and made of a soft plastic for conforming receipt in the auditory canal of the helmet wearer and an adaptor piece of solid material containing an earplug receiver, an amplifier, and an energy source;

the transmitting device and the earplug receiver being located adjacent each other and defining a wireless transmission path there between, whereby, signals representative of auditory signals received by the receiving device are transmitted interference free to the earplug receiver and without substantial enlargement of the external profile of the helmet shell.

9. A hearing device according to claim 8, wherein the transmitting device is an infra-red transmitter and the earplug receiver is an infra-red sensitive receiver; a cavity is formed within the thickness of the shell material and opens to the interior of the helmet, the receiving and transmitting devices are mounted in the cavity with the transmitting device aligned with the opening, an annular elastic cushion is mounted on the inside surface of a portion of the shell surrounding the opening for encircling, cushioning pressure engagement with the adaptor piece to retain the attachment piece positioned in the auditory canal of the wearer and to cushion the wearers ear so that the infra-red transmission path extends from the transmitting device through the cavity opening and a central aperture of the annular cushion to the earplug receiver, whereby, interference free transmission of the auditory signals can be effected.

10. A hearing device for a protective helmet, comprising: an auditory signal receiving device and a wireless transmitting device mounted on a shell of the helmet; an earplug including an earphone and a wireless earplug receiver said earphone being positionable in an auditory canal of the helmet wearer, said wireless transmitting device and said wireless earplug receiver being positioned spaced apart from each other defining a wireless transmission path therebetween, whereby signals representative of auditory signals received by the receiving device are transmitted to the earplug receiver without connection between the earplug receiver and the transmitting device.

* * * * *